United States Patent [19]

Stahr

[11] 4,314,027
[45] Feb. 2, 1982

[54] METHOD OF DETECTING MOLD TOXIN INFECTED GRAINS

[75] Inventor: Henry M. Stahr, Ames, Iowa

[73] Assignee: Iowa State University Research Foundation, Inc., Ames, Iowa

[21] Appl. No.: 170,726

[22] Filed: Jul. 21, 1980

[51] Int. Cl.³ ............................................. B01D 15/08
[52] U.S. Cl. .................................... 435/34; 23/232 C; 55/67; 55/386; 435/30
[58] Field of Search ....................... 55/67, 386; 435/30, 435/34; 422/70; 23/232 C

[56] References Cited

U.S. PATENT DOCUMENTS

| 3,374,660 | 3/1968 | McKinney | 23/232 C |
| 3,690,837 | 9/1972 | Witz et al. | 435/30 |
| 3,791,522 | 2/1974 | Eisenbeiss | 55/386 X |
| 3,815,405 | 6/1974 | Dravnieks | 23/232 C |
| 3,980,524 | 9/1976 | Reuter | 435/34 |
| 4,003,257 | 1/1977 | Fletcher | 55/67 X |
| 4,004,881 | 1/1977 | Ligon, Jr. | 23/232 C |

OTHER PUBLICATIONS

Fast Screening Method for Determination of Aflatoxin Contamination in Cottonseed Products by Cucullu et al. Reprint from the Journal of Official Analytical Chemist, vol. 55, 9/1972 and addendum.

Primary Examiner—John Adee
Attorney, Agent, or Firm—Zarley, McKee, Thomte, Voorhees & Sease

[57] ABSTRACT

A method of detecting mold toxin infected grains. The method involves obtaining a gaseous sample from the grain which is representative of the volatiles which are produced within the grain, and thereafter determining by gas chromatographic analysis of said gaseous sample, if the grain contains volatiles known to be produced by mold toxin infected grains.

4 Claims, 4 Drawing Figures

METHOD OF DETECTING MOLD TOXIN INFECTED GRAINS

BACKGROUND OF THE INVENTION

Present methods of determining important characteristics of grain as it moves in transit from the farm to commercial market, are crude at best. Most involve utilization of mechanical grain probes. As the grain is sold from the grower to the intermediate grain broker, the price to a certain extent is determined by an examination of the characteristics of the grain. That is to say, moisture content, the amount of adulterating foreign materials, and the like. In most instances, the testing is done by utilization of either hand grain probes or auto-mechanical probes. In either event, the testing is done in essentially the same manner. The probe is thrust into the load of grain and a sample extracted. Thereafter, the sample is analyzed to determine moisture content and visually inspected for adulteration. These inspections are not only time consuming, but many times can be inaccurate. For example, visual inspection is perhaps the most common way of determining the presence of mold toxin, along with smelling. However, the mere fact that a sample does not look moldy or does not have a moldy smell, does not necessarily mean that the grain is not infected with mold toxins.

Certainly other more sensitive mold toxin tests could be utilized, but they are simply not practical for use at a grain elevator where the testing must be done quickly and oftentimes by a fairly non-skilled operator.

There is therefore a continuing need for on-site testing methods and an apparatus for determining grain quality. This invention has as its primary objective, a fulfilling of that need.

In particular, an object of this invention to provide a method of detecting mold toxin infected grains which correlates the presence or absence of mold toxins with the presence or absence of certain volatiles in the grain.

Another object of this invention is to provide a method of detecting the presence or absence of mold toxins in grain which employs a gas chromatograph analysis technique.

Yet another object of this invention is to provide a simple apparatus; that is to say, a volatiles trapping capsule which can be inserted into a kit type gas chromatograph and quickly determined instrumentally to detect the presence or absence of volatile materials known to be present in moldy grains.

An even further object of this invention is to provide a detection system for detection of mold infected grain which is highly sensitive, even sensitive to as low as at the sub-microgram level, which is much lower than the level capable of detection by smell.

The method and manner of achieving each of the above objectives and fulfilling the needs as stated, will become apparent from the detailed description of the invention which follows hereinafter.

SUMMARY OF THE INVENTION

Figure 1:
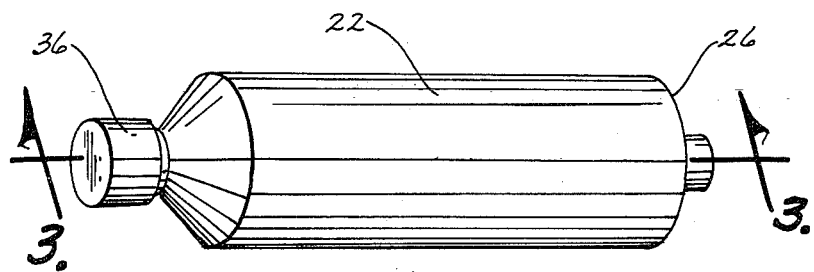
FIG. 1 is a perspective view of this injector.
Figure 2:
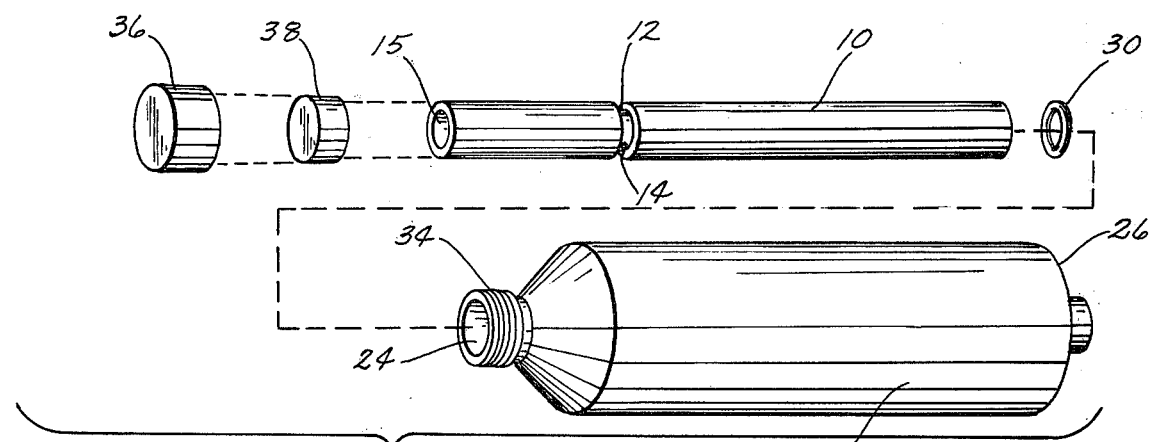
FIG. 2 is an exploded perspective view showing the injection capsule and the injector.
Figure 3:
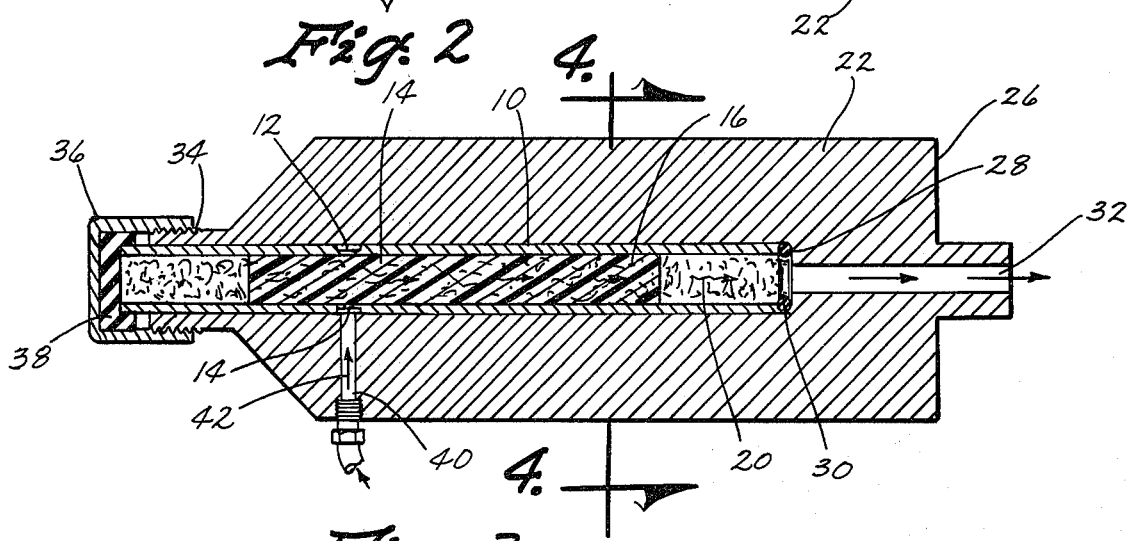
FIG. 3 is a sectional view along line 3—3 of FIG. 1 showing the injector with the injection capsule mounted therewithin.
Figure 4:
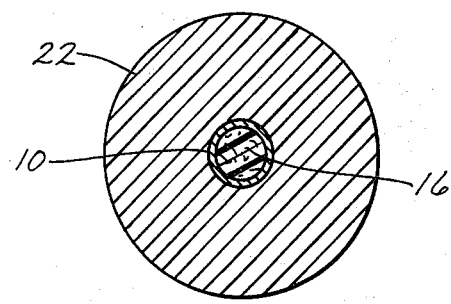
FIG. 4 is a sectional view along line 4—4 of FIG. 3.

A quick, easy and efficient method of determining the likelihood of grain being infected with mold toxins. Mold and mycotoxin growth in grains are often associated with a moldy or musty odor. These odors have been examined and found to contain certain volatile materials. The volatile materials are therefore stripped from a grain and gas chromatographically analyzed to detect the presence or absence of those compounds known to be associated with moldy odors. Also, a convenient injection capsule and injector for quick determination of the presence or absence of the tested for volatile compounds is provided.

DETAILED DESCRIPTION OF THE INVENTION

As heretofore mentioned, the primary objective of the present invention is to make objective, rapid data available for control of mold contamination in grain commerce. The present invention involves a pattern recognition process for determining which grains in commerce are most likely to be infected with mold and mycotoxins.

In the past, visual inspections and smell have largely been used to sort out potential offending grain loads. However, such systems, as one would expect, are inaccurate and at best rather crude, and lack sensitivity.

In accordance with the present invention, an analysis of causation factors for moldy odor is known mold and mycotoxin infected grains has provided a new detection system. In particular in no case where known mold toxins were present in cereal grains in highly concentrated form, did the grain not have a "moldy odor" associated with the grain. Samples of the grain have therefore been tested, analyzed and determined in an effort to find the causation factor for the moldy odor.

After studying many grain samples, it has been determined that certain common patterns appear when analyzing known moldy samples. In particular, if the volatiles are extracted from such samples and analyzed, there is a large abundance of $C_7$, $C_8$, and $C_9$ volatile compounds. These compounds are predominantly alcohols, aldehydes and ketones. It is this correlation that has allowed the determination of the test procedure of the present invention.

A highly positive correlation has been found between the presence of these volatile compounds and mold infected grains. That is to say, when the conditions of moisture and heat are proper in the field, spores which are present grow and produce the molds. The molds in turn produce mycotoxins. It is these mycotoxins that have the musty odor and are characterized by a predominance of $C_7$, $C_8$, and $C_9$ aldehyde, ketone and alcohol volatiles.

While some of these volatiles have in the past been known to be associated with moldy grains, no one has developed a simple, efficient, reliable and easy to perform test utilizing this pattern recognition system for detecting moldy grains. Work in the past has involved grinding of the grains, solvent extraction and thereafter testing. Also some steam distillation work has been done. But none of these are practical for people employed in the grain commerce industry to adopt. The present tests are time consuming, require skilled operators and fairly extensive, and expensive, equipment and know-how. In the present invention instruments and methods requiring much skilled know-how, are avoided.

In accordance with the first step, a sample of grain to be tested for the presence of mycotoxins is obtained in the conventional manner.

The sample is then vacuum stripped to remove gaseous volatiles. This may or may not be accompanied by heating. However, testing of numerous samples has shown that while heating does increase the amount of volatiles extracted, even at room temperature sufficient amounts are extracted in order to allow the detection system to work.

In accordance with the vacuum stripping process, a sample to be tested is selected and placed in a vacuum chamber of conventional construction.

Placed in series in sealing relationship with the line of the vacuum chamber is the injection capsule 10. The injection capsule 10 is a hollow cylindrical tubular member. It has a milled annular notch 12 and a side aperture 14 which communicates with the internal bore 15 thereof. The central portion of injection capsule 10 is filled with a gas absorbing medium 16. Gas absorbing medium 16 may be a variety of conventional materials such as one sold under the trademark Porapak Resin. Such materials are well known and basically are column packing materials, and often may consist of a styrene divinyl benzene polymer resin. Porapak Q is one resin material which is preferred. The end portions 18 and 20 are filled with a more porous material such as glass wool. The Porapak Q resin utilized herein is manufactured by Waters Associates and is sold as a 100/120 mesh resin material. Other polymeric gas absorbent materials could, of course, be used. The ends of injection capsule or cartridge 10 are open.

It is this injection cartridge 10 which is placed in line, in series, and sealing relationship with the vacuum line. The vacuum line, or vacuum oven, is pulled with a vacuum sufficient to draw volatile vapors away from the grain test sample. The vacuum need not be a particularly strong one, and a vacuum of 29 inches of mercury absolute has been found sufficient in most instances.

The time for pulling of the vacuum is not critical and from one minute to three minutes is generally sufficient. When the vacuum is pulled on the sample, volatiles, if any present with the grain sample, are pulled away and carried through the vacuum line. Since the injection capsule 10 is in series with the vacuum line, the volatiles are pulled therethrough. Any of the contaminating volatiles known to be associated with mold which are present, are absorbed upon the polymeric gas absorbing resin 16 and retained thereon.

After the injection cartridge 10 has been used to absorb volatiles which are vacuum stripped from the grain sample, the cartridge 10 is then ready to be used for gas chromatographic analysis. Cartridge 10 is then removed from its series line relationship with the vacuum chamber and inserted into injector 22.

Injector 22 is designed to be used in conjunction with a conventional gas chromatograph (not depicted). Injector 22 is comprised of a cylindrical container having an annular bore 24. Annular bore 24 is of such a size that cartridge 10 will matingly fit therewithin. Near the forward end 26 of injector 22 a shoulder 28 is provided. Shoulder 28 provides a seating for O-ring 30. Forward of O-ring 30 annular bore 24 decreases in diameter as depicted at exit opening 32.

At the rear of injector 22 a threaded neck 34 is provided. Cap 36 is threadably received on neck 34. At the interior of cap 36 at its top is provided a rubber seal 38.

When cap 36 is threadably received on neck 34 with cartridge 10 placed in bore 24, compression forces are provided and the cartridge is sealingly pushed against O-ring 30.

Injector 22 is provided at its rearward end with a side port opening 40. Side port opening 40 is located so that it is adjacent annular groove 12.

The injector 22 and injector cartridge 10 are used in the following manner. The cartridge 10, after being used for vacuum stripping of a grain sample to absorb the volatiles on gas absorbing resin 16, is placed in annular bore 24. Cap 36 is tightened. Thereafter, the injector 22 containing the cartridge 10 is placed in the injection port opening of a gas chromatograph. Carrier gas, such as nitrogen, is pumped through opening 40 as depicted via arrow 42, through opening 14 in annular groove 12 and from there to the interior of the injection cartridge 10. It passes downwardly through injection cartridge 10 as depicted at 44 and out through injector exit 32 into the gas chromatograph injection port. If the sample contains the volatiles indicative of moldy grain, the gas chromatograph will record this result and the operator can visually see in a matter of moments, that the grain is likely to be contaminated with mycotoxins.

The following examples are offered to further illustrate, but not limit, the process of the invention.

EXAMPLE

In the following examples, 100 gram samples of corn were tested. A first sample was a sample of South Carolina field corn known to be aflatoxin infected. Other samples were used on a control basis wherein the mold was actually grown in the laboratory by innoculating corn with *Aspergillus flavus* mold. Other samples known to be non-contaminated were obtained from a cooperative feed mill.

Each of the samples, comprising a 100 gram test sample, were vacuum stripped to obtain a gaseous sample of the volatiles present, if any. They were stripped in the following manner. The sample was placed in a flask which was placed in line with a vacuum oven. A vacuum was pulled at 29 inches of mercury absolute. Placed in line with the vacuum downstream from the sample containing flask was an injector cartridge 10 filled with Porapak Q in the middle and glass wool 18 adjacent the ends. The vacuum was pulled on the sample for 120 minutes. This allowed, with the aid of the portable vacuum as described herein, the collection of volatiles from the grain sample. Some were collected at ambient temperature and others were collected at slightly elevated temperatures of 100°.

After collection of the volatiles which were passed through the in-series line injector cartridge 10, the cartridges 10 containing the volatiles which were absorbed, were then placed in the injector 22 which was then placed in communication with the injection port for a gas chromatograph.

The volatile chemical entities trapped onto the gas absorbent 16 were then analyzed in the gas chromatograph to determine the presence or absence of $C_7$, $C_8$, and $C_9$ alcohol, ketone and aldehyde volatiles normally indicative of the presence of mycotoxins. The field samples from South Carolina, and the laboratory grown samples both known to be aflatoxin infected, showed peaks in the gas chromatograph analysis at levels indicating the presence of 1 Octanol, cis 2 octene-1-Ol, $C_7$ and $C_9$ aldehydes and ketones.

Further, samples were run having levels of aflatoxin so low that a musty odor was not detectable by humans. Even with these samples, the aflatoxin contaminated grain was detectable even when the toxin was at such low levels as one microgram. Sampling times of 5 minutes were sufficient with samples containing 1 microgram of octanol.

It can therefore be seen that a highly efficient and useful mold detection analysis system has been provided. All that need be provided for use in testing at the grain elevator is a kit containing the injection cartridge 10, the injector 22, a vacuum stripper and a small gas chromatograph indicator. The sample is simply vacuum stripped and the absorbed volatiles on the cartridge 10, if any, are then tested by placing in the injector 22. A readout is provided on the gas chromatograph indicating whether the offending $C_7$, $C_8$ and $C_9$ volatiles are present and they can be compared with a standard chart showing the readings if the offending volatiles are present. If they are, grain can be rejected as mycotoxin containing.

What is claimed is:

1. A pattern recognition method of detecting mold and fungal infected grains, comprising:

stripping a gaseous sample from the grain which is representative of volatiles which are produced within the grain, collecting said gaseous sample volatiles on a gas absorbing substance, determining by gas chromatographic analysis if said gaseous samples contain $C_7$ to $C_9$ aldehyde, alcohol or ketone volatiles known to be produced by fungal and mold species, in infected grains.

2. The method of claim 1 wherein said gas absorbing substance is thereafter gas chromatographically analyzed.

3. The method of claim 2 wherein said gas absorbing substance is a polymeric gas absorbing material.

4. An apparatus for gas analysis of volatiles stripped from test grain samples, said apparatus comprising, a cylindrical cartridge having first and second ends having near said first end an annular groove, said annular groove having a port extending to the interior of said cylindrical cartridge, with the interior portion of said cartridge being filled with the gas absorbing material, and an injector container for holding said cartridge, said injector container having an opening which allows flushing of inert gas through said opening, and through the opening in said injector cartridge to pass through said gas absorbing material, and means in association with said second end of said cylindrical cartridge to provide a sealing relationship between said second end of said cylindrical cartridge and said injector container.

* * * * *